United States Patent [19]

Christiansen et al.

[11] Patent Number: 4,619,660

[45] Date of Patent: Oct. 28, 1986

[54] COMPRESSIBLE ROTATIONAL ARTIFICIAL JOINT

[76] Inventors: Jean E. Christiansen, 15 Westwood Rd. South, Massapequa Park, N.Y. 11762; Maryanne Fitzgerald, 19 Brown Pl., Red Bank, N.J. 07701; Mitchell G. Moeller, 4938 Ten Mills Rd., Columbia, Md. 21044; Artemis Pascalides, P.O. Box 4488, Washington, D.C. 20017; R. Thaddeus Vayda, 3051 Mimon Rd., Annapolis, Md. 21403

[21] Appl. No.: 661,105

[22] Filed: Oct. 15, 1984

[51] Int. Cl.⁴ .............................................. A61F 2/64
[52] U.S. Cl. ..................................................... 623/46
[58] Field of Search ........................ 3/22, 26, 2, 27, 28, 3/29; 272/114; 135/82, 84, 86

[56] References Cited

U.S. PATENT DOCUMENTS 2,859,451  11/1958  Mauch ........................................ 3/22
4,051,558  10/1977  Vallatton ..................................... 3/29

FOREIGN PATENT DOCUMENTS 880960  10/1961  United Kingdom .................. 135/82

Primary Examiner—Richard J. Apley
Assistant Examiner—James Prizant
Attorney, Agent, or Firm—Donald C. Lepiane

[57] ABSTRACT

An artificial knee has a shock casing and a hinge sheath. Plungers mounted in the shock casing bias the casing and sheath away from each other as a shock absorber mounted in the shock casing controls movement and absorbs shock of the casing and sheath as they move relative to one another. A stem secured to the shock casing passes through the hinge sheath into holes in the roller bearing. In this manner with the sheath and casing are urged toward one another by applying weight to the knee as in walking or kneeling, the stem end moves into the roller bearing to prevent movement of the artificial leg secured to the roller bearing.

19 Claims, 6 Drawing Figures

COMPRESSIBLE ROTATIONAL ARTIFICIAL JOINT

BACKGROUND OF THE INVENTION

1. Field of the Invention

This invention relates to an artificial replacement for a body joint and, more particularly, to an artificial knee.

2. Discussion of the Technical Problem

Individuals who lose limbs as a result of degenertive diseases or accidents are provided with artificial limbs in order that the individuals have some degree of mobility. Artificial limbs or replacements for body parts date back to about 600 B.C. for peg legs and to the sixteenth century for hook hands.

In the instance where the individual has above the knee amputation, prosthetic limb preferably supports the body while providing some degree of mobility. At present, artificial legs are capable of supporting body weight but provide little if any mobility.

It would be advantageous therefore to provide an artificial joint e.g. an artificial knee that is capable of supporting body weight while providing mobility.

SUMMARY OF THE INVENTION

This invention relates to an artificial joint e.g. a compressible rotational artificial knee. The artificial knee has a first housing attachable to the leg portion above the knee remaining after amputation and a second housing attachable to a rigid member substituted for the amputated leg portion below the knee. The first and second housings are biased away from each other and are provided with facilities for controlling the rate of displacement of the first and second housings toward one another and for absorbing shock. A member is rotatably mounted in the second housing and is attachable to the rigid member substituted for the leg portion. Locking facilities responsive to the first and second housings moving toward one another lock the rotatable member in position e.g. with the rigid member in an extended position similar to a leg supporting weight during walking or standing.

DETAILED DESCRIPTION OF THE INVENTION

Figure 1:
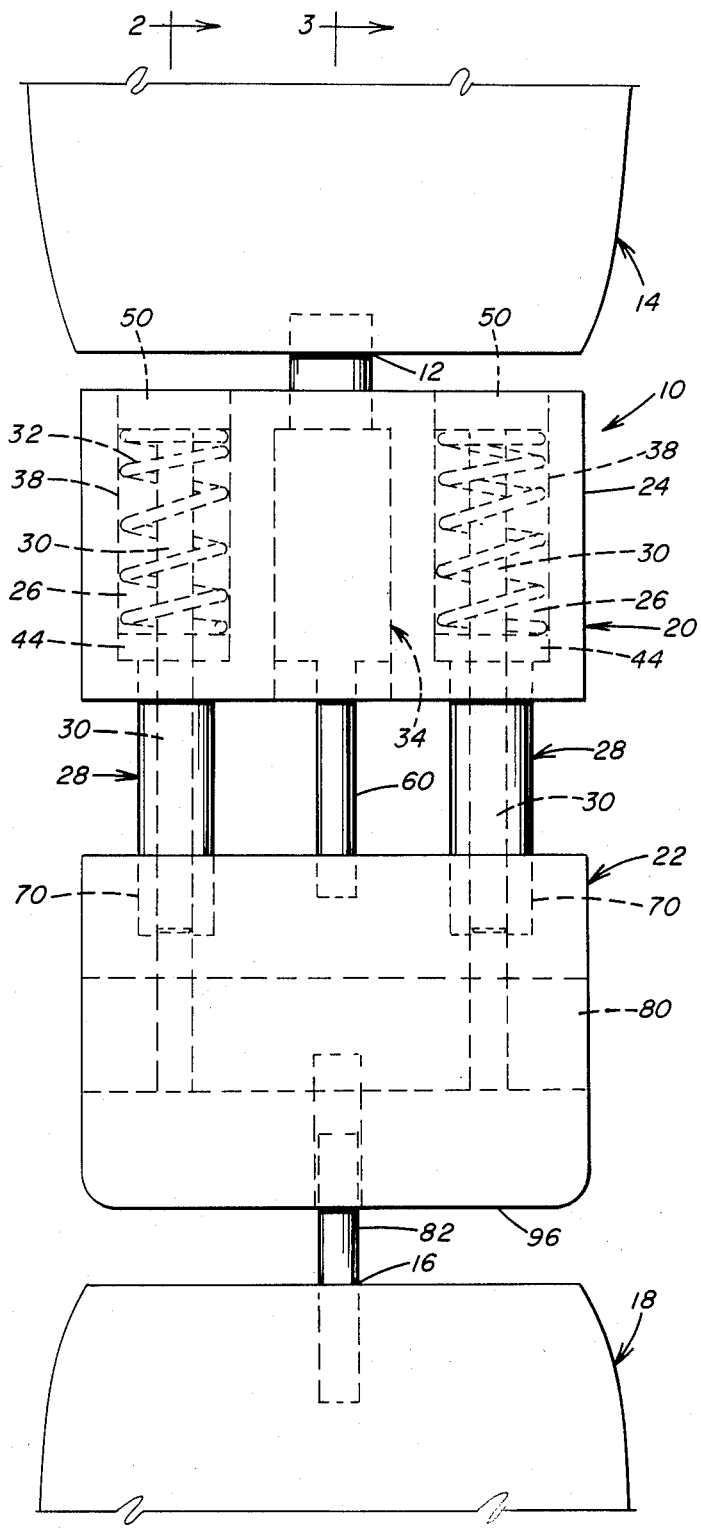
FIG. 1 is a front elevated view of an artificial knee embodying features of the invention illustrated in a non-weight supporting position.

Referring to FIG. 1 there is shown artificial knee 10, incorporating feature of the invention, connected at 12 to a harness 14 and at 16 to a rigid member 18. The harness 14, rigid member 18 and techniques for connecting same to the artificial knee 10 are not limiting to the invention. The harness 14 may be any convenient type for securing a prosthetic limb to the portion of the leg remaining after amputation. The rigid member 18 may be any convenient type for supporting body weight e.g. a steel or wooden member.

Figure 2:
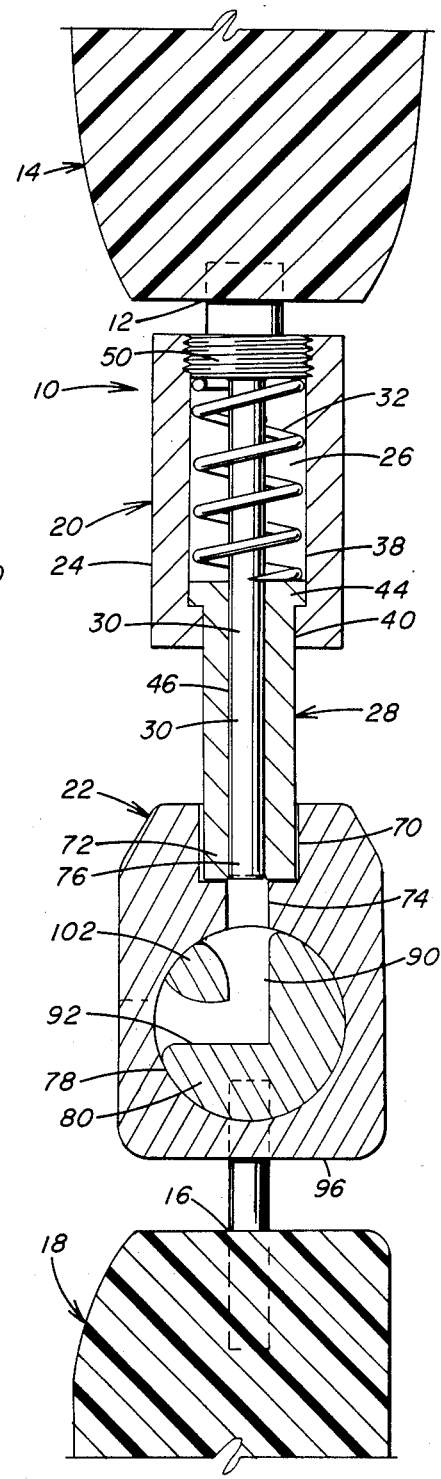
FIG. 2 is a view taken along lines 2—2 of FIG. 1.
Figure 3:
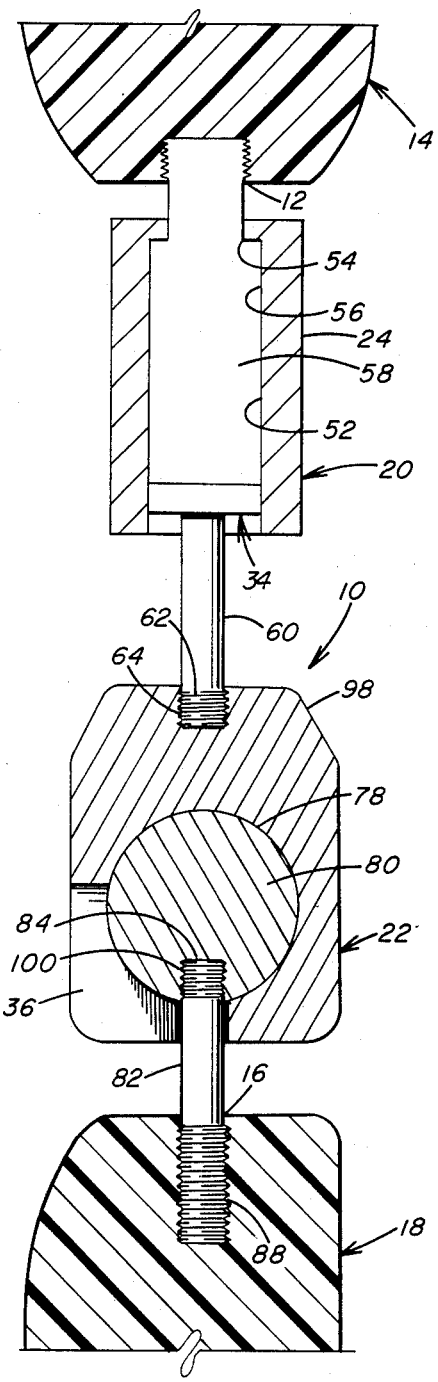
FIG. 3 is a view taken along lines 3—3 of FIG. 1.

The knee 10 includes a shock casing 20 connected to a hinge sheath 22 in a manner to be discussed below. With reference now to FIGS. 1-3, the casing 20 includes a housing 24 having a pair of chambers 26 each having a plunger 28 captured therein and slideable on stem 30. The plunger 28 is biased downward as viewed in FIG. 2 in any convenient manner e.g. by spring 32. A member 34 for preferably controlling rate of displacement of the shock casing 20 and hinge sheath 22 relative to each other and for damping shock during such displacement has one end connected to the hinge sheath 22 and the other end connected to the harness 14 at 12.

Figure 4:
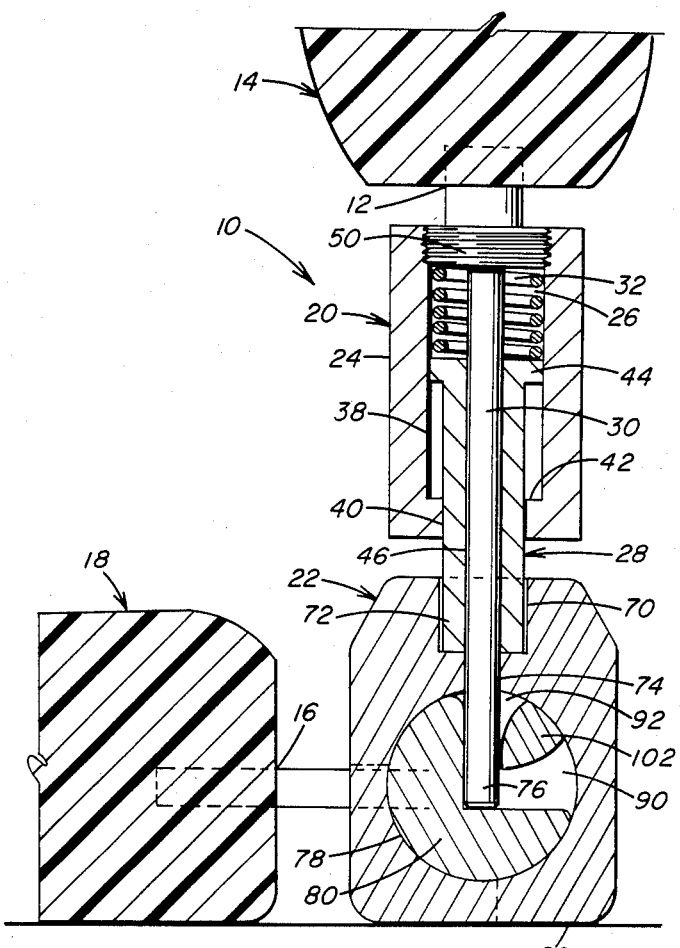
FIG. 4 is a view similar to the view of FIG. 2 illustrating the artificial knee of the invention in a kneeling weight supporting position.

A shock casing 20 incorporating features of the invention had the elements constructed of plastic e.g. nylon, synthetic resin polymers sold undmer the trademark TEFLON, of delrin unless indicated otherwise. The shock casing 20 included a housing 24 having a height as viewed in FIG. 1 of about 3 11/16 inches (9.4 centimeters (cm)), a length as viewed in FIG. 1 of about 4 inches (10.1 cm), and a width as viewed in FIG. 2 of about 1⅜ inches (3.5 cm). Each of the chambers 26 has an upper circular opening 38 having a diameter of about 1 inch (2.54 cm) for a depth of about 3¼ inches (8.26 cm) and thereafter a lower circular opening 40 having a diameter of about ¾ inch (1.92 cm) to form a ledge 42 (numbered only in FIG. 4). The plungers each have a length of about 2½ inches (12.35 cm) with an upper circular portion having a diameter of about 1 inch (2.54 cm) for a legnth of about ⅜ inch (0.96 cm) and thereafter a diameter of about ¾ inch (1.92 cm) to provide the plungers with a head 44 which engages its respective ledge 42 preventing the plunger 28 from escaping its respective chamber 26 at one end of the housing 24. The plungers 28 each have a center bore 46 clearly shown in FIG. 4 having a diameter of about ⅜ inch (0.96 cm) and extending through its length for slideably receiving the stem 30. The stem 30 has a diameter of about ⅜ inch (0.96 cm) and a length of about 4 inches (10.16 cm). One end of the stem 30 is provided with threads (not shown) about 1.4 inch (0.64 cm) along its length for securing the stem 30 to cap 50. The cap 50 has a diameter of about 1 inch (2.54 cm) and a length of about ½ inch (1.27 cm) with threads on its outside surface to secure the cap 50 in the upper end of its respective chamber 26 as shown in FIGS. 1, 2 and 4.

Referring now to FIG. 3, the shock casing 20 further includes a center passage 52 having an upper portion 54 having a diameter of about ½ inch (1.27 cm) for a length of about ¼ inch (0.64 cm) and a lower portion 56 of a diameter of about 1⅛ inches (2.86 cm) for the remainder of the length of the passageway 52. An adjustable air shock 58 of the type sold by Taylor Device Inc. Model No. PS-1 is mounted in the center passageway 52. The threaded end of the shock absorber 58 passes through the upper portion 54 of the passageway 52 and is connected at 12 to the harness 14. Piston rod 60 of the shock absorber 58 has its end 62 threaded into hole 64 in the hinge sheath 22.

Figure 6:
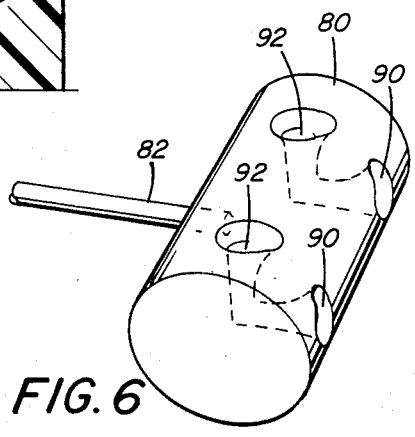
FIG. 6 is an isometric view of a roller bearing incorporating feature of the invention.
Figure 5:
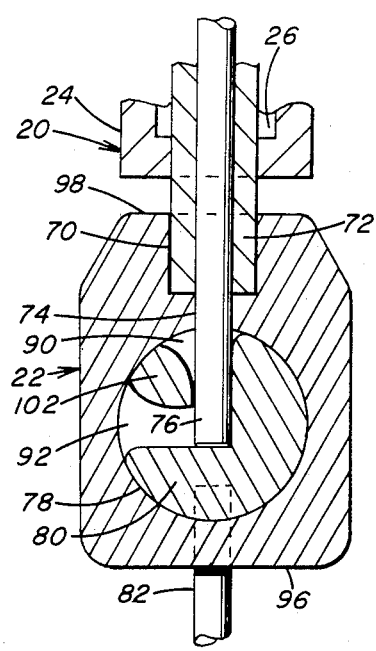
FIG. 5 is a fragmented view of the lower portion of the artificial knee of the instant invention illustrating the knee in an upright weight supporting position.

The hinge sheath 22, as shown in FIGS. 1-3, has a pair of upper holes 70 for receiving end portion 72 of the plungers 28 and lower holes 74 for receiving end portion 76 of the stems 30. The lower holes 74 terminate at longitudinal passageway 78 which slideably receives a roller bearing 80 see also FIG. 6. The roller bearing 80 is captured in the passageway 78 by a shaft 82 having one end 84, as clearly shown in FIG. 3, passing through slot 86 and secured to the roller bearing 80 with the other end 88 secured to the rigid member or artificial lower leg 18. With reference now to FIGS. 4-6, the roller bearing 80 has a first and second pair of holes 90 and 92 respectively (only one hole of each pair shown) in FIGS. 4 and 5 alignable with the holes 74 of the hinge sheath 22 as shown in FIG. 1. The holes 92 of the roller bearing 80 receive the end portion 76 of the stem 30 as shown in FIG. 4 during kneeling each in a manner discussed below.

A hinge sheath 22 constructed in accordance to the invention for use with the shock casing 20 described above was made of plastic, (e.g., nylon, synthetic resin polymers sold under the trademark TEFLON, or delrin) unless indicated otherwise. The hing sheath 22 included a housing having a length of about 4 inches (10.1 cm), and a height of about 2¾ inches (6.99 cm) as viewed in FIG. 1 and a width of about 1⅜ inches (3.08 cm) at the lower surface 96 for a height of about 1¾ inches (3.92 cm) and thereafter decreases in width for a length of about 1 inch (2.54 cm) to provide the top of surface 98 with a width of about 1 inch (2.54 cm) as clearly shown in FIGS. 2-5. The holes 70 (see FIG. 1) are on a center to center spacing of about 1¾ inches (4.46 cm) and on a center to adjacent wall spacing of about 1⅛ inches (2.86 cm) and each have a diameter of about ⅔ inch (1.68 cm) for a length of about ½ inch (1.27 cm) for receiving the end porton 72 of its respective plunger 28. The lower holes 74 have a diameter of about ⅜ inch (0.84 cm) for a length of about ½ inch (1.27 cm) for receiving the end portion 76 of its respective stem 30. The lower holes 74, as shown in FIGS. 2, 4, and 5, terminate in the longitudinal passageway 78 having a diameter of about 1½ inches (3.71 cm). The slot 86 having a width of about 1 inch (2.54 cm) is formed in the hinge sheath 22 and as shown in FIG. 3 has a height of 1⅝ inches (4.13 cm) and a length of about ⅞ inch (1.96 cm).

With reference to FIGS. 4-6, the roller bearing 80 has a diamter of about 1½ inches (3.18 cm) and a length of about 4 1/16 inches (9.1 cm). A hole 100, shown only in FIG. 3, having a diameter of about 1 inch (2.54 cm) and a depth of about ½ inch (1.27 cm) in the roller bearing 80 is aligned with the slot 86. The two pairs of holes 90 and 92 in the roller bearing 80 are each on a center to center spacing of about 1¾ inches (4.46 cm) and on a center to adjacent end of about 1 3/32 inches (2.9 cm) with adjacent ones of holes 90 and 92 offset from each other by 90 degrees. The holes 90 and 92 are alignable with respective ones of the holes 74 (see FIGS. 4 and 5). The holes 90 and 92 as shown in FIGS. 4 and 5 have enlarged receiving end portions 102 for guiding the end portion 76 of the stem 30 into the holes 90 or 92 as is discussed below.

The artificial knee 10 of the invention having the above described shock casing 20 and hinge sheath 22 can be assembled in the following manner. With reference to FIG. 3, the shock absorber 58 has its end threaded through the center passageway 52 of the shock casing 20 and end 62 of the rod 60 threaded into center hole 64 of the hinge sheath 22. The upper holes 70 of the hinge sheath 22 are aligned with the lower circular outlet portions or holes 40 of the shock casing 20 as shown in FIG. 4 for one pair of holes 70 and 74. A plunger 20 is inserted into each of the chambers 26 with end portons 72 of the plungers 20 passing out of the shock casing 20 into respective holes 70 of the hinge sheath 22. A spring 32 is mounted in each chamber 26 against the head 44 of the plunger 28. The cap 50 having the stem 30 is moved into a chamber 26 through the spring 32 and into and through the center bore 46 of the plunger 28. The spring 32 was made of steel and had an uncompressed length of about 3 inches (7.62 cm). When compressed in the chamber by securing the cap 50 in position each spring exerted a force of about 70 pounds (31 kilograms) on its respective plunger 28 to bias the shock casing 20 and hinge sheath 22 away from each other. The plungers 28 in their respective hole 70 prevent rotation of the casing 20 and sheath 22 relative to one another. The roller bearing 80 is inserted into the passageway 78. The upper end of the shaft 82 is threaded into the hole 100 of the roller bearing 80. The threaded portion of the shock absorber 58 is threaded into the harness 14 at 12 and the rigid member 18 is threaded onto the end 88 of the shaft 82.

As the person walks, the artificial knee 10 is raised. The springs 32 bias the hinge sheath 22 away from the shock casing 20 to maintain the end portion 76 of the stem 30 out of the roller bearing holes 90 or 92. As the knee 10 is moved forward for a step the rigid member or lower leg 18 moves outward to rotate the roller bearing 80 to move the shaft 82 against wall portion 102 of the slot as shown in FIG. 3. Weight is applied to the artificial knee 10 and as shown in FIG. 5 the weight moves the shock casing 20 downward toward the shock casing 22. The shock absorber 58 takes up the shock while controlling movement of the hinge sheath 22 toward the shock casing 20. Movement of the casing and sheath toward each other urges the plungers 28 upward into their respective chambers 26 against the biasing action of the spring 32 moving the end 76 of the stems 30 into the holes 90 to lock the knee 10 in position as shown in FIG. 5.

As weight is removed from the artificial knee 10, e.g., as the next step is taken, the springs 32 urge the plungers 28 downward as viewed in FIGS. 1, 2 and 4 to move the hinge sheath 22 away from the shock casing 20 and to move the ends 76 of the stems 30 out of the holes 90 of the roller bearing 80. The shock absorber 58 controls the rate of displacement of the hinge sheath 22 away from the shock casing 20. The knee is now ready for the next step.

With reference to FIG. 4, when the person kneels, weight is removed from the artificial knee and the knee moves toward the ground to rotate the roller bearing 80. After the knee 10 engages the ground, weight is applied to the knee 10 to move the plungers 80 into their respective chambers against the biasing action of the spring 32. The end portion 76 of the stem 30 moves into the holes 92 as previously discussed for the holes 90. In the position shown in FIG. 4 the roller bearing 80 is locked. In addition, insertion of the end 76 of the stem 30 into the holes 92 of the bearing 80 provides for compression of the artificial knee to simulate compression of the human knee. In this manner the person does not lean to one side thereby reducing pressure on the hip.

As can be appreciated the invention is not limited to the above example which was presented for illustration purposes only.

What is claimed is:

1. An artificial joint comprising:
   a first housing having a pair of chambers;
   a pair of plungers;
   means for capturing one of said plungers in one of said chambers;

means for biasing end portion of said plunger out of its respective chamber;
a second housing;
a roller bearing mounted in said second housing;
means mounted in said first housing and engageable with said roller bearing for securing said roller bearing in one of a plurality of positions; and
shock absorbing means for controlling movement of said housings toward one another against said plungers to move said plunger into said first housing against biasing action of said biasing means and for moving said securing means into engagement with said roller bearing to limit movement of said roller bearing.

2. The artificial joint as set forth in claim 1 wherein the biasing action of said biasing means is sufficient to move said first and second housings away from each other against the action of said shock absorbing means.

3. The artificial joint as set forth in claim 2 wherein said joint is a knee and said securing means includes:
a first and second pair of holes in said roller bearing;
a pair of holes in said second housing and aligned with the first pair of holes of said roller bearing when said roller bearing is in a first position and aligned with the second pair of holes of said roller bearing when said roller bearing is in a second positon.

4. The artificial knee as set forth in claim 3 wherein said securing means includes a pair of stems secured to said first housing and aligned with one of said pair of holes in said second housings wherein displacement of said housings toward one another moves the stem through the pair of holes in said second housings in one of said pair of holes in said roller bearing aligned therewith.

5. The artificial knee as set forth in claim 4 wherein a stem is mounted in each of said chambers passing through said plunger in said chamber and said holes in said second housing each have a first opening for receiving said end of said plunger and a smaller hole portion for receiving passing said stem.

6. The artifical knee as set forth in claim 1 wherein said second housing has a plurality of holes, whrein said shock absorbing means is mounted in said first housing and has one end extending beyond said first housing and piston end of said shock absorber secured to the second housing, and wherein said plunger end in said holes of said second housing prevent rotation of said first and second housing relative to one another while providing movement toward and away from each other.

7. An artificial joint comprising:
a first housing;
a second housing;
rotating means mounted in said second housing wherein said rotating means includes a roller bearing;
means mounted in said first housing and acting on second housing for biasing said first and second housings away from one another along a substantially linear path;
shock absorbing means mounted in said first housing and acting on said second housing to absorb shock as said first and second housings move along the linear path toward one another toward a first position; and
means mounted in said first housing and engaging said rotating means for locking said rotating means in a selected position when said housings are in the first position, wherein said locking means includes at least one hole in said roller bearing.

8. The artificial joint as set forth in claim 7 wherein said biasing means include:
a pair of chambers in said first housing;
a plunger in each said chambers wherein said plunger is slideable in it respective chamber to move one end of said plunger out of said first housing against said second housing; and
a spring captured in each of said chamber to bias the end of said plunger out of its respective chamber against said second housing to move the housings away from each other.

9. The artificial joint as set forth in claim 8 wherein said locking means includes a first and second pair of holes in said roller bearing and a stem passing through each of said chambers, through said respective plunger in said chamber out of said first housing and into said second housing, wherein movement of said housings toward one another moves end portion of said stems into holes of said pair of holes aligned with said stem.

10. The artificial joint as set forth in claim 9 wherein said joint is a knee and a first pair of said holes is aligned with said stem when the knee simulates a kneeling position and a second pair of said holes aligned with the stem when the knee simulates an upright or waking position.

11. The artificial knee as set forth in claim 10 wherein the first housing in secured to harness means and said roller bearing is connectable to lower portons of an artificial leg.

12. An artifical joint comprising:
a first housing;
a second housing;
rotating means in said second housing;
means mounting said first and second housings for movement of said first and second housings toward each other into a first position and away from each other into a second position, said movement being along a substantially linear path; and
means acting on said rotating means for limiting movement of said rotating means when said first and second housings are in said first position and for permitting movement of said rotating means when said first and second housings are in the second positon.

13. The joint as set forth in claim 12 wherein said movement means includes biasing means mounted in at least one of said housings.

14. The joint as set forth in claim 13 wherein said biasing means includes:
a pair of plungers each mounted in a chamber of said first housing;
a spring associated with each of said plungers for biasing said plungers out of said first housing against said second housing to urge said housings away from each other.

15. The joint as set forth in claim 12 further including means for controlling rate of displacement of said first and second housings toward and away from each other.

16. The joint as set forth in claim 15 wherein said controlling means includes a shock absorber mounted in said first housing and having its piston connected to said second housing.

17. The joint as set forth in claim 12 wherein said limiting means includes a shaft passing through said second housing and engaging said rotating means when said housings are in the first position to limit rotation of said rotating means.

18. The joint as set forth in claim 17 wherein said rotating means is a roller bearing and said limiting means includes a hole in said roller bearing for receiving a portion of said shaft.

19. The joint as set forth in claim 18 wherein a portion of said shaft is mounted in said first housing and an opposite portion slideable in said second housing, wherein movement of said housings toward one another moves the shaft portion through the second housing into the said roller bearing.

* * * * *